United States Patent
Zupon

(10) Patent No.: US 11,331,162 B2
(45) Date of Patent: May 17, 2022

(54) SURFACE MARKERS FOR 3D SUPINE AUTOMATED ULTRASOUND IMAGING AND USE THEREOF

(71) Applicant: IMAGING FOR WOMEN, L.L.C., Kansas City, MO (US)

(72) Inventor: Allison Zupon, Kansas City, MO (US)

(73) Assignee: Imaging for Women, L.L.C., Kansas City, MO (US)

( * ) Notice: Subject to any disclaimer, the term of this patent is extended or adjusted under 35 U.S.C. 154(b) by 125 days.

(21) Appl. No.: 16/741,448

(22) Filed: Jan. 13, 2020

(65) Prior Publication Data

US 2021/0212795 A1  Jul. 15, 2021

(51) Int. Cl.
   *A61B 90/00* (2016.01)
   *A61B 8/08* (2006.01)

(52) U.S. Cl.
   CPC ............ *A61B 90/39* (2016.02); *A61B 8/0825* (2013.01); *A61B 8/483* (2013.01); *A61B 2090/3908* (2016.02); *A61B 2090/3925* (2016.02); *A61B 2090/3991* (2016.02)

(58) Field of Classification Search
   None
   See application file for complete search history.

(56) References Cited

U.S. PATENT DOCUMENTS

| 5,873,827 A | 2/1999 | Russell |
| 9,439,621 B2 | 9/2016 | Zhang et al. |
| 2005/0080333 A1 | 4/2005 | Piron et al. |
| 2015/0294495 A1 | 10/2015 | Nielsen et al. |
| 2015/0297316 A1* | 10/2015 | Grinstaff ................ A61B 10/04 600/414 |
| 2018/0214106 A1 | 8/2018 | Wang et al. |
| 2018/0271484 A1* | 9/2018 | Whisler ............... A61B 8/4444 |
| 2019/0000318 A1 | 1/2019 | Caluser |

FOREIGN PATENT DOCUMENTS

| CN | 108420458 A | 8/2018 | |
| WO | WO-2005117711 A2 * | 12/2005 | ........... A61B 8/0825 |

OTHER PUBLICATIONS

PDC; SPEE-D-MARK Mammography Skin Markders [Brochure], 9 pages, Feb. 12, 2020, Web page retrieved from https://www.pdchealthcare.com/products/mammography-products/skin-markers-mammography.html.

Xact—"Order Samples [Brochure]," 3 pages, Feb. 12, 2020, Web page retrieved from https://xactmarkers.com/order-samples/.

* cited by examiner

*Primary Examiner* — Amanda Lauritzen Moher
*Assistant Examiner* — Delia M. Appiah Mensah
(74) *Attorney, Agent, or Firm* — Polsinelli PC

(57) ABSTRACT

Provided herein are methods of documenting breast tissue in an area of interest in a subject in need thereof using automated breast ultrasound. The methods comprise using surface markers that can clearly identify the area of interest in a resulting 3-D image without introducing artifacts that obscure the tissue intended for examination.

14 Claims, 8 Drawing Sheets

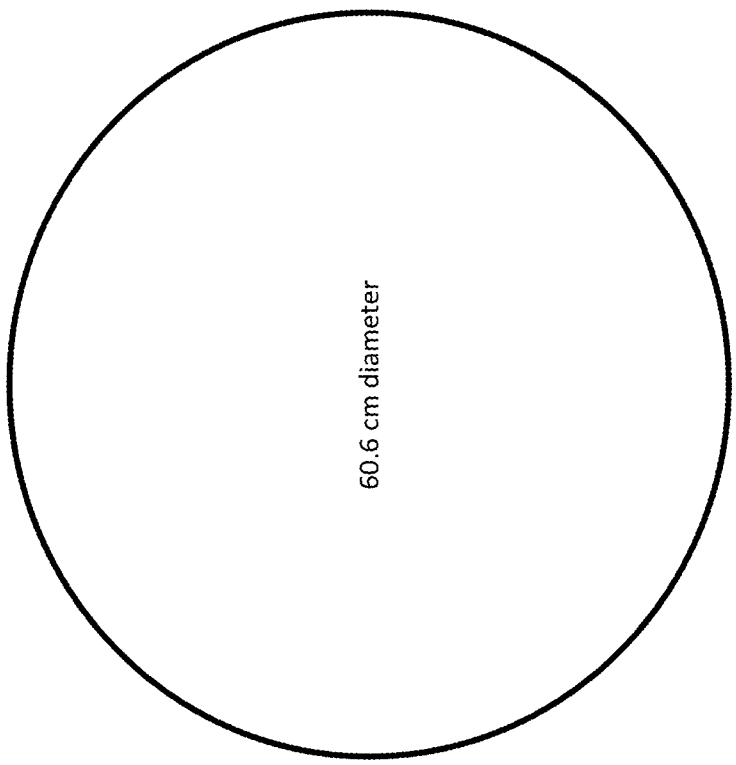
FIG. 5A
FIG. 5B

SURFACE MARKERS FOR 3D SUPINE AUTOMATED ULTRASOUND IMAGING AND USE THEREOF

FIELD OF THE INVENTION

The present invention generally relates to the field of medical imaging of the breast, and in particular, to the methods of documenting breast tissue in a subject in need thereof using automated breast ultrasound.

BACKGROUND OF THE INVENTION

Breast mammography has become the standard diagnostic breast screening tool in women's healthcare, aiding in the detection and intervention of early-stage breast cancers. However, despite favorable research, mammography alone has not been effective in all populations of women and is most notably less sensitive in women who have dense breast tissue. Dense breast tissue obscures tumors on mammograms, making it difficult for radiologists to read and interpret the exams. This inaccuracy has resulted in an increased number of false negatives that lead to missed diagnosis of an existing cancer, and has increased healthcare costs and patient anxiety.

For this reason, and the fact that women with dense breast tissue are at an increased risk for developing breast cancer, supplemental imaging tests have become popular, including ultrasound imaging. However, there are limitations to using traditional hand-held ultrasound that have prevented the technology from being used more extensively in supplemental breast imaging for women with dense breast tissue. The length of traditional ultrasound tests is one drawback, as it can take up to 30 minutes to complete the exam. Another issue that handheld ultrasound screening presents is operator dependency. The results obtained in an ultrasound exam are highly dependent on the skill and expertise of the operator. Further, results obtained using handheld ultrasound are difficult to compare year after year, as only 5 images of each breast (one per quadrant and the subareolar breast) are saved in a typical exam.

3D Supine Automated Ultrasound (3D SAUS) technology addresses the shortcomings of traditional ultrasound. Like traditional ultrasound, 3D SAUS uses high-frequency sound waves targeted at the breast, but the scans are automatically acquired in a short period with no or minimal operator input, thereby greatly reducing operator dependency. Further, 3D SAUS provides physicians with an ultrasonic three-dimensional (3-D) volumetric image of the entire breast, allowing experts the ability to document the breast from a variety of angles and offer unambiguous analysis, with the added ability to perform year to year comparison of imaging results.

Despite these advantages, challenges in documenting an area of interest when an automated system is used remain. In breast imaging, it is important to designate a palpable or painful area for the radiologist to document the correct area and to record the information for the patient's record. Using traditional ultrasonography, only the area of interest is imaged, and the tissue of interest is marked on the images by the sonologist or physician performing a handheld evaluation. In non-operator dependent 3D SAUS imaging, an operator cannot designate the area of interest, and the sonologist or physician cannot then document the correct area.

Therefore, there is a need in the medical field of breast imaging for a method of designating an area of interest in breast tissue for later analysis and diagnosis of the palpable and/or painful area.

SUMMARY OF THE INVENTION

One aspect of the present disclosure encompasses a method of documenting breast tissue of interest in a subject in need thereof using automated breast ultrasound. The method comprises placing a marker having a flat configuration with an upper side and a lower side at the surface of the breast at a location designating the breast tissue of interest, wherein the lower side of the marker is in contact with the surface of the breast. The method further comprises acquiring an ultrasonic 3-D volumetric image of the breast by applying sound waves to the breast including the marker and the breast tissue of interest; identifying a sonographic outline of the marker at the surface of the breast in the acquired image, wherein the outline results from artifacts produced by the marker of a portion of the sound waves applied to the breast; identifying the breast tissue of interest in the image in reference to the outline of the marker at the surface of the breast, wherein the tissue of interest is breast tissue underlying the surface of the breast at the location of the marker; and documenting the breast tissue of interest.

The tissue of interest can comprise a palpable mass, and the subject can be a human with dense breast tissue. The intensity of the outline of the marker at the surface of the breast in the acquired image can be of uniform intensity. Further, the artifact can result in an area of increased brightness in the acquired image.

The marker can comprise material uniformly distributed throughout the marker. The tissue of interest can be substantially free of artifacts in the image. The configuration of the marker can comprise material, width, and thickness. The material can be plastic material, the width of the marker can range from about 0.3 cm to about 1 cm, and the thickness of the marker ranges from about 0.5 mm to about 2 mm. In some aspects, the marker is in the form of a circle, and the diameter of the circle ranges from about 0.3 cm to about 1 cm. The marker can be free of openings, bends, curves, lumps, indentations, or irregularities. The marker can further comprise means for retaining the marker in a fixed position at the surface of the breast.

Another aspect of the present disclosure encompasses a method of using a surface marker for documenting a palpable mass in breast tissue in an area of interest of a subject in need thereof using automated breast ultrasound. The method comprises placing a plastic marker having a flat configuration with an upper side and a lower side, a width ranging from about 0.3 cm to about 1 cm, and a thickness ranging from about 0.5 mm to about 2 mm, at the surface of the breast at a location designating the breast tissue of interest, wherein the lower side of the marker is in contact with the surface of the breast. The method further comprises acquiring an ultrasonic 3-D volumetric image of the breast by applying sound waves to the breast including the marker and the breast tissue of interest; identifying a sonographic outline of the marker at the surface of the breast in the acquired image, wherein the outline of the marker results from artifacts produced by the marker of a portion of the sound waves applied to the breast; identifying the breast tissue of interest in the image in reference to the outline of the marker at the surface of the breast, wherein the tissue of interest is breast tissue underlying the surface of the breast at the location of the marker; and documenting the breast tissue of interest.

Yet another aspect of the present disclosure encompasses a method of using a surface marker for documenting a palpable mass in breast tissue in an area of interest of a subject in need thereof using automated breast ultrasound. The method comprises placing a circular plastic marker having a flat configuration with an upper side and a lower side, a diameter ranging from about 0.3 cm to about 1 cm, and a thickness ranging from about 0.5 mm to about 2 mm, at the surface of the breast at a location designating the breast tissue of interest, wherein the lower side of the marker is in contact with the surface of the breast. The method further comprises acquiring an ultrasonic 3-D volumetric image of the breast by applying sound waves to the breast including the marker and the breast tissue of interest; identifying a sonographic outline of the marker at the surface of the breast in the acquired image, wherein the outline of the marker results from artifacts produced by the marker of a portion of the sound waves applied to the breast; identifying the breast tissue of interest in the image in reference to the outline of the marker at the surface of the breast, wherein the tissue of interest is breast tissue underlying the surface of the breast at the location of the marker; and documenting the breast tissue of interest.

Other aspects and features of the disclosure are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 5A depicts a side perspective view of one aspect of the marker.

FIG. 5B depicts a top view of one aspect of the marker.

DETAILED DESCRIPTION

Figure 1B:
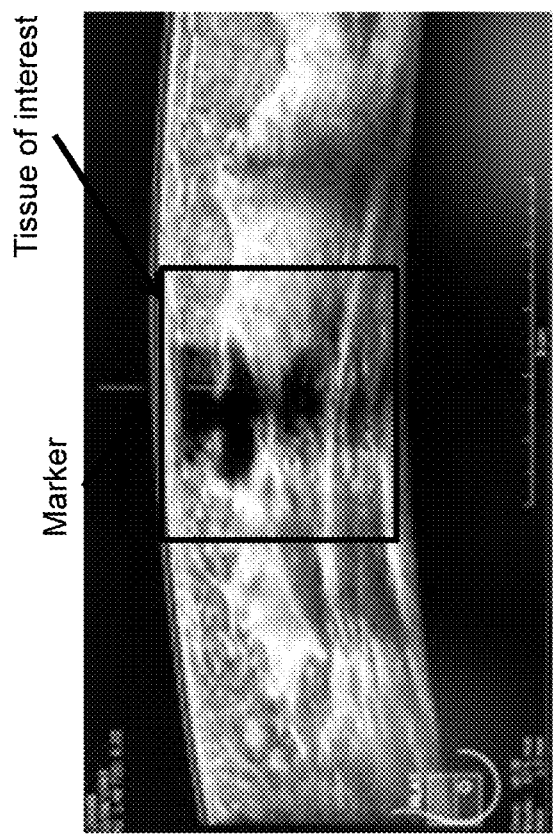
FIG. 1B shows a 3-D ultrasound image of a breast having a palpable mass acquired using 3D SAUS. A 2 mm thick vinyl disc was used to designate the tissue of interest (TOI). The image is a transverse or acquisition plane image of the breast. The tissue of interest is marked. Crosshairs designate the location of the marker.

The present invention generally relates to methods of documenting breast tissue of clinical interest in ultrasonic 3-D volumetric images acquired using automated breast ultrasound (3D SAUS) technology. The methods comprise placing markers on the surface of the breast at a location designating the tissue of interest (TOI) and acquiring the 3-D image for later documentation by a sonologist, technologist, or physician. Importantly, markers of the disclosure can identify the TOI in the 3-D images without introducing any significant distortions that obscure the tissue intended for examination, allowing for clear documentation of the tissue.

I. Methods

In one aspect, the present disclosure encompasses a method of using a surface marker for documenting a TOI in breast tissue of a subject in need thereof. The TOI can be any tissue in the breast where a clear sonographic image is desired. For instance, the TOI can be breast tissue of clinical interest. A TOI can be an area of the breast comprising an abnormality such as a palpable mass, an area of pain reported by the subject, an area identified as indeterminate or suspicious on mammography, an area of scarring from prior surgery, an area related or adjacent to the abnormality, or combinations thereof. An area related to an abnormality can be similar appearing masses observed during bilateral breast ultrasound evaluation. Bilateral breast ultrasound evaluation can be an important tool, as multiple similar appearing masses are less suspicious than a single mass. Demonstrating multiple similar bilateral masses can help a physician determine if the palpable finding is benign, sparing the cost of biopsy and follow-up. An area adjacent to the abnormality can be the remainder of dense breast tissue which can be screened for occult cancer.

The subject is a human in need of 3-D sonographic evaluation. A human subject in need of 3-D sonographic evaluation can have TOI as described above. Dense breast tissue can obscure a palpable mass when imaged using X-ray mammography, as both the dense breast tissue and other abnormalities can appear white. Conversely, sonographic images can differentiate between the dense breast tissue and an abnormality in a TOI. Dense breast tissue in images acquired using sonography appears white, and some abnormalities, such as malignant tumors, most often appear gray. Therefore, a subject can be a human with dense breast tissue and a TOI in need of further visualization and evaluation.

The method comprises placing a marker on the surface of a breast at a location designating the TOI to be documented. In general, the marker is placed on the surface of the breast adjacent to or above the TOI. An individual of skill in the art will recognize the location on the surface of the breast most suitable for placing the marker to designate the TOI. Alternatively, the patient can place the marker in the area of pain or palpable fullness. The marker has a flat configuration with an upper side and a lower side. The marker is placed at the surface of the breast at a location designating the breast tissue of interest, wherein the lower side of the marker is in contact with the surface of the breast.

A 3-D ultrasound image is acquired using an 3D SAUS imaging method and device. As such, the marker is used in conjunction with standard 3D SAUS equipment to image the breast. The image is acquired by applying sound waves to the breast including the marker and the breast tissue. Methods of acquiring a 3-D ultrasound image using 3D SAUS are known in the art and can be performed by a trained technician.

The method comprises identifying a sonographic outline of the marker at the surface of the breast in the acquired image. The outline of the marker results from artifacts resulting from attenuation or enhancement by the marker of a portion of the sound waves applied to the marker. Artifacts produced by the marker are further described in Section II below.

The method further comprises identifying the breast TOI in the image. The TOI is identified by referencing the tissue to the outline of the marker at the surface of the breast. In the coronal image of the breast, the TOI is breast tissue underlying the surface of the breast at the location of the marker.

As it is further explained below, the surface marker fails to introduce significant distortions in the TOI in the imaged breast. Further, any significant artifacts that may be introduced by the marker into the breast tissue in the image can be difficult to discern from various types and confirmations of breast tissue. Therefore, it may not be possible to identify the TOI in an acquired image by identifying artifacts in the 3-D image of the TOI. Instead, the TOI is identified in reference to the outline of the marker in the 3-D image. More specifically, TOI is breast tissue underlying the surface of the breast at the location of the outline of the marker in the 3-D image.

The method further comprises documenting the TOI. As used herein, the term "documenting" refers to examining the 3-D image of the breast to evaluate the TOI, for example, by a physician. Methods of documenting breast tissue in a 3-D image acquired by 3D SAUS are known in the art and can be performed by a skilled individual, such as a sonologist, a trained technician, a researcher, or a physician. For instance, documenting the breast tissue may comprise identifying conformations of various tissue types in the breast. Additionally, documenting the breast tissue may comprise identifying and diagnosing a malignant or benign mass, dense breast tissue or other breast tissue, identifying scar tissue, identifying irregular breast tissue such as a palpable mass, and identifying bilateral masses. Importantly, because the marker fails to introduce significant distortions in the TOI, the method allows for unambiguous documentation of the TOI, thereby allowing the patient and physician to feel confident that the TOI was scrutinized. It also allows the physician to have a record of the specific location the patient asked to have evaluated for future reference.

In another aspect, the disclosure encompasses a method of using a marker for documenting an area of interest in breast tissue of a subject in need thereof using 3D SAUS. The method is as described in this section above.

II. Surface Markers

Markers currently in use in X-ray mammography interfere with sound waves in ultrasound imaging and produce unacceptable distortions that obscure the tissue to be examined by ultrasound. Conversely, markers of the disclosure produce an image with minimal or no distortions for unambiguous documentation of the tissue.

As explained in Section I above, an outline of the marker is located in the acquired image of the breast. The outline can result from differences in attenuation or enhancement (posterior acoustic enhancement) of a portion of the sound waves applied to the breast, including the marker. A marker can attenuate or enhance sound waves to result in an area of decerased or increased brightness in the acquired image, respectively. The marker can attenuate or enhance no more than about 50%, 40%, 30%, 20%, 10%, or about 1% of the sound waves applied to the marker. The marker can also attenuate or enhance no more than about 10%, 9%, 8%, 7%, 6%, 5%, 4%, 3%, 2%, or 1% of the sound waves applied to the marker, or no more than about 1%, 0.5%, or 0.1% of the sound waves applied to the marker. In some aspects, the marker attenuates or enhances a sufficient amount of sound waves to produce an outline visible on the surface of the breast in the ultrasound image. In some aspects, the marker attenuates or enhances sound waves uniformly throughout the marker.

The composition and thickness of the marker, as well as other physical characteristics such as size and shape, can and will vary, and are selected to provide the beneficial qualities of the marker. In other words, the physical characteristics of the marker are selected to produce a sonographic outline of the marker in a 3-D image of a breast acquired by 3D SAUS, all without introducing any distrotions that obscure the tissue intended for examination, allowing for unambiguous documentation of the TOI.

In some aspects, the composition and thickness of the marker are substantially uniform throughout the marker. In other words, the marker does not comprise composition and/or thickness irregularities on the surface of the marker, or in the body of the marker. The uniformity of composition and thickness of the marker generates artifacts of uniform intensity in the 3-D image. In one aspect, the marker is as depicted in FIG. 5.

The marker has a flat configuration, and can be of any overall size and shape. For example, the marker can be circular, rectangular, diamond-shaped, or other suitable shapes. In some aspects, the marker comprises a flat surface free of openings, bends, curves, or irregularities. In some aspects, the marker is circular.

The marker can be of any thickness, provided the physical and beneficial characteristics of the marker are preserved. The thickness of the marker can be less than 0.5 mm or can range from about 0.001 mm to about 5 mm. In some aspects, the thickness of the marker ranges from about 0.5 mm to about 2 mm. In some aspects, the thickness of the marker is substantially uniform throughout the marker.

The marker can be any width provided a sonographic outline of the marker can be located in the acquired image and provided the marker does not introduce distortions in the imaged TOI. The width of the marker can range from about 0.1 cm to about 5 cm, or about 0.3 cm to about 1 cm. In some aspects, the width of the marker corresponds to the size of the tissue of clinical interest. For instance, the width of the marker can be of a relatively similar, smaller, or larger size as a tissue of clinical interest to be imaged. In some aspects, the marker is in the form of a circle, and the diameter of the circle can range from about 0.1 cm to about 5 cm, or about 0.3 cm to about 1 cm.

In some aspects, appropriate material for a marker can be a plastic material. Plastics are organic polymers of high molecular mass and can also contain other substances. Plastics can be synthetic, most commonly derived from petrochemicals, or made from renewable materials such as polylactic acid from corn or cellulosics from cotton linters. Non-limiting examples of plastics include acrylic, acrylonitrile butadiene styrene (ABS), nylon, polylactic acid (PLA), polybenzimidazole, polycarbonate, polyether sulfone, polyoxymethylene, polyetherether ketone, polyetherimide, polyethylene, polyphenylene oxide, polyphenylene sulfide, polypropylene, polystyrene, polyvinyl chloride, olyvinylidene fluoride, Teflon, and combinations thereof. Other suitable materials can be paper and cardboard. Suitable material for a marker can be determined experimentally.

The material and thickness of the marker, as well as other physical characteristics such as size and shape, are also compatible with 3D SAUS equipment and procedure used during the acquisition of the 3-D image. In general, the physical characteristics of the marker can and will vary depending on the 3D SAUS equipment used to acquire the 3-D images, and the TOI or abnormalities in the TOI to be documented, among other variables. For instance, during ultrasound examination, including 3D SAUS examination, a layer of gel can be applied to the surface of the skin above the tissue area of interest and a transducer is put in contact with the skin to acquire the images. The procedure may further comprise the use of a harness that covers the breast before imaging. Therefore, the marker is also compatible with the environment presented by the gel and/or harness, durable enough to withstand repeated physical contact with the transducer head while the technologist is performing the ultrasound examination, and avoids the possibility that the marker will interfere with the function of the equipment.

The marker can further comprise means for retaining the marker in a fixed position on the surface of the breast when acquiring the 3-D ultrasound image. The means can be a layer of adhesive on one or both sides of the marker to affix the marker to the skin. The adhesive may be any adhesive typically employed in clinical applications. However, the adhesive is compatible with the 3D SAUS equipment and procedure used during the acquisition of the 3-D image by the 3D SAUS equipment. For instance, an aqueous gel is typically applied to the surface of the skin to remove air and provide a bond between the skin and the transducer. Therefore, the adhesive is capable of retaining the marker on the surface of the breast when an aqueous gel is applied to the surface of the skin. In addition, the adhesive bond must have sufficient strength to withstand repeated mechanical contact between the marker and a 3D SAUS device during sonography. Of course, the marker can be affixed to the skin by other means without departing from the scope of the invention. For example, a separate piece of water-insoluble tape dimensioned to be substantially co-extensive with the marker could be used to hold the marker in place. Alternatively, the means can be a part of the device. For instance, when a 3D SAUS technique comprises the use of a holster to hold the breast in position, the marker can be retained in a fixed position by the holster by placing the marker in direct contact with the breast under the holster.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a," "an," "the" and "said" are intended to mean that there are one or more of the elements. The terms "comprising," "including," and "having" are intended to be inclusive and mean that there may be additional elements other than the listed elements.

As various changes could be made in the above-described markers and methods without departing from the scope of the invention, it is intended that all matter contained in the above description and in the examples given below, shall be interpreted as illustrative and not in a limiting sense.

The term "comprising" means "including, but not necessarily limited to;" it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

The terms "area of interest" and "tissue of interest" are used interchangeable, and refer to breast tissue in need of documentation using sonographic imaging.

As used herein, the term "flat" refers to a smooth and even surface, without marked openings, bends, curves, irregularities, lumps, or indentations.

As used herein, the term "artifact" refers to an enhancement or attenuation of sound waves at the marker or the tissue of interest by the marker that can be observed in an ultrasound image.

As used herein, the term "distortion(s)" refers to an enhancement or attenuation of sound waves at the tissue of interest by the marker that can be observed in an ultrasound image, wherein the distortions obscure the tissue to be examined, thereby preventing documentation of a TOI of interest.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. 3D SAUS Imaging and Documentation of a Palpable Mass Using a Marker Prepared from Thick Vinyl Material A patient presented with breast pain and a possible palpable mass. A mammogram was negative but demonstrated dense breast tissue. A 3-D ultrasound image was generated to evaluate/document the palpable mass. The images were very clear, but it was not possible to identify the area because the 3-D image was obtained using 3D SAUS, where the operator cannot provide input on the location of the mass in relation to the palpated area. Further, no marker was used to identify the location of the palpable mass.

In an attempt to identify markers appropriate for 3D SAUS imaging, a number of materials were used to prepare the markers. In one attempt, a metallic BB marker was placed on the palpable area and secured with medical tape, as is the practice during mammography. However, the tape left a large area of distortion in the image, obscuring tissue and precluding satisfactory evaluation of the image.

Figure 1A:
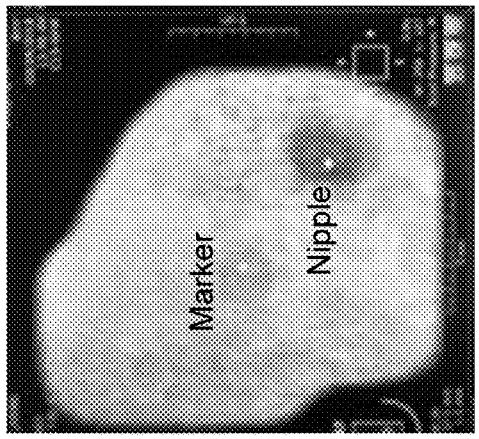
FIG. 1A shows a 3-D ultrasound image of a breast having a palpable mass acquired using 3D SAUS. A 2 mm thick vinyl disc was used to designate the tissue of interest (TOI). The image is at the skin surface of the breast in the reconstructed coronal plane. Software-generated dots designate the nipple and the marker. An outline cast by the marker placed on the surface of the breast is also visible. Crosshairs placed by the reading physician during interpretation designate the location of the marker.

In another attempt, a marker made of a clear 0.6 cm thick vinyl material was used during 3D SAUS imaging of the breast of a subject with a palpable mass. The marker was visible at the surface of the breast in the 3-D image, clearly marking the area of interest, but produced unacceptable results, casting distortions in the image at the area of interest, and obscuring the TOI to be examined (FIG. 1A). Darker areas noted in FIG. 1B represent unacceptable distortions that obscure the TOI.

Figure 2A:
FIG. 2A shows a 3-D ultrasound image of a breast having a mammography marker used for indicating a TOI. The image is of the breast at the skin surface in the reconstructed coronal plane with three mammogram markers designated by colored arrows. The nipple is marked with a computer-generated yellow dot. Crosshairs placed by the reading physician designate the location of the breast tissue of interest. Blue arrow: Triangular shaped mammogram marker. Green arrow: Circle-shaped mammogram marker. Purple arrow: arrowhead-shaped marker.
Figure 2B:
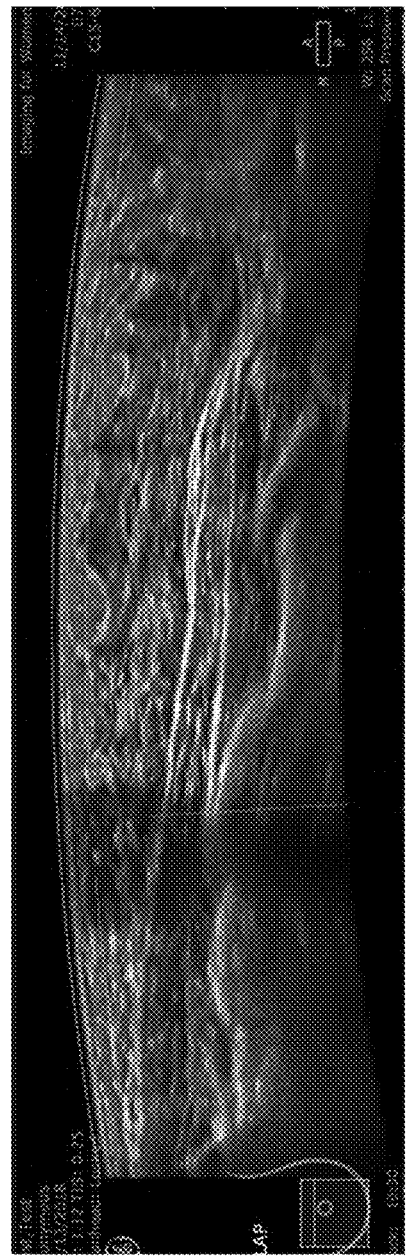
FIG. 2B shows a 3-D ultrasound image of a breast having a mammography marker used for indicating a TOI. The image is a transverse or acquisition plane image of the breast showing the tissue of interest in the breast. Crosshairs placed by the reading physician designate the location of the breast tissue of interest.

Example 2. 3D SAUS Imaging and Documentation of a Palpable Mass Using Mammography Markers In another attempt, markers normally used during mammography were used during 3D SAUS imaging of a breast. The markers are standard mammogram markers comprised of a thin rim of shaped metal, within an adhesive strip. Three markers, each having a defined shape, triangular, circular, or arrowhead, were used. Outlines of the shaped metallic markers and the adhesive strip, seen as dark or hypoechoic areas, can be seen in FIG. 2A. Transverse or acquisition plane image of the breast imaged in FIG. 2B at the location of the marker shows that distortions from the metallic mammogram marker unacceptably obscures the view of the TOI (crosshairs).

Figure 3A:
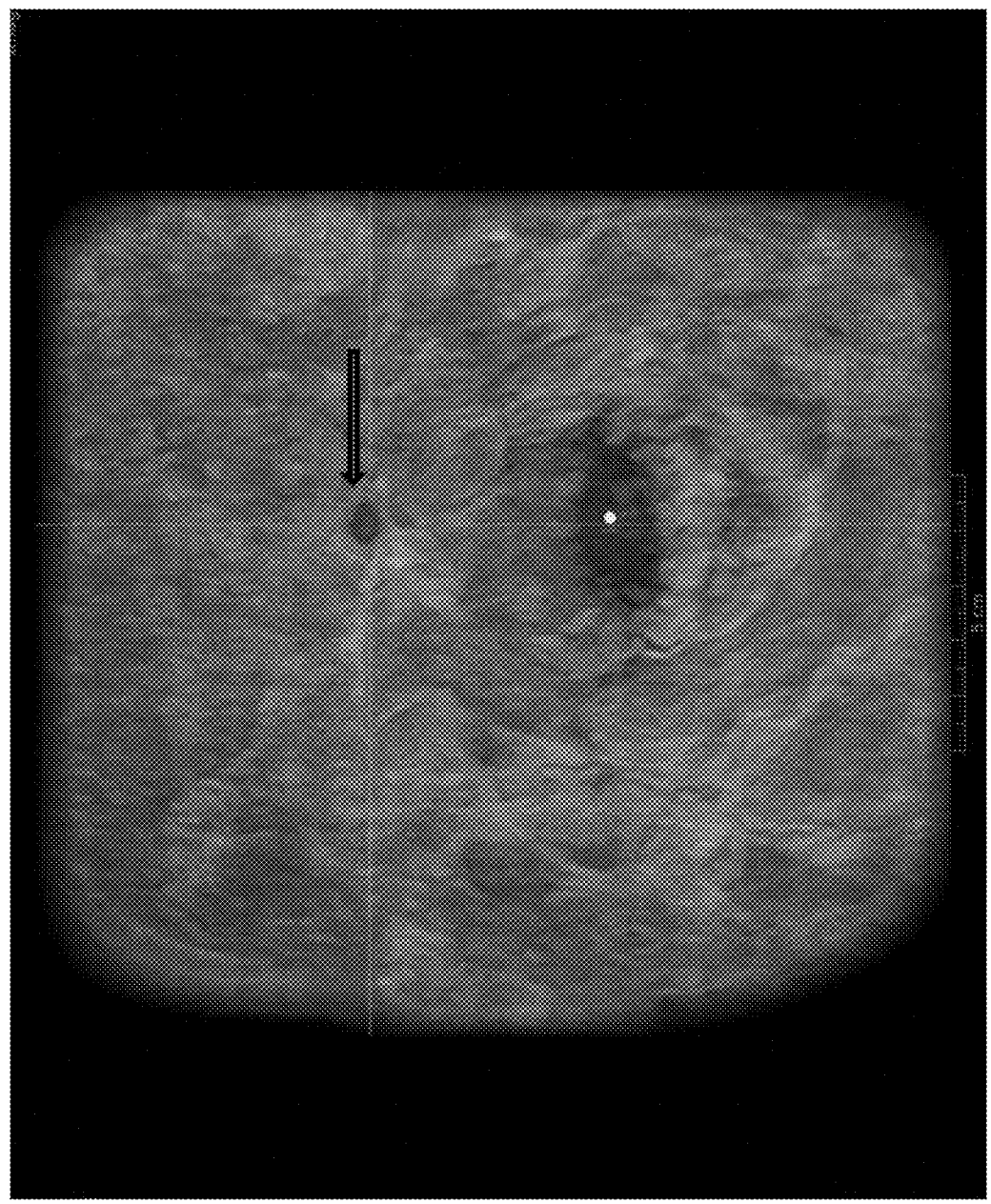
FIG. 3A depicts a coronal image of a breast having a marker of the disclosure designating an area of interest. The coronal image is at the skin surface showing a visible outline of the surface marker of the invention (blue arrow), designating the TOI. Also seen are blue and green crosshairs placed by the reading physician during interpretation and the software-generated yellow dot nipple marker. Crosshairs indicate the same location on the breast.
Figure 3B:
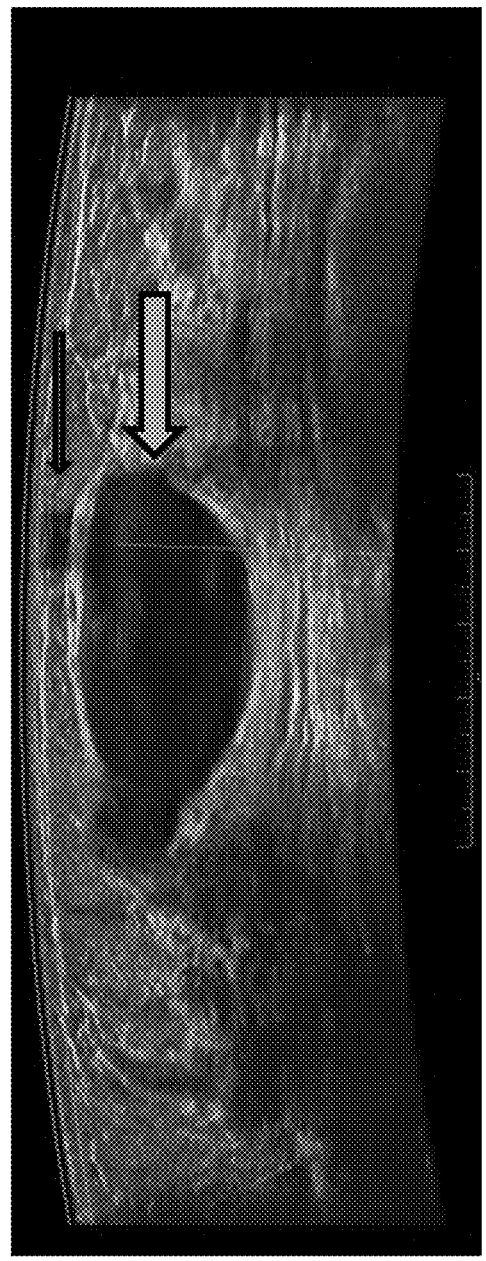
FIG. 3B depicts a transverse or acquisition plane image of the breast shown in FIG. 3A having a marker of the disclosure designating an area of interest. The image shows a thin artifact (blue arrow) extending from the location of the marker on the surface of the breast just below the surface of the skin. A benign cyst (Orange arrow) is visible in the image. Crosshairs indicate the same location on the breast.

Example 3. 3D SAUS Imaging and Documentation of a Palpable Mass Using a Marker of the Disclosure A marker prepared using thin clear plastic material was then used to image the breast of a subject. The marker was circular in shape, with a diameter of 0.6 cm and a uniform thickness of 0.1 cm (FIG. 5A and FIG. 5B). The marker was visible at the surface of the breast in the coronal image (FIG. 3A; blue arrow), clearly marking the area of interest. The marker did not obscure the area of interest (FIG. 3A; crosshairs). Transverse or acquisition plane image of the same breast at the tissue of interest under the marker as designated by the crosshairs (FIG. 3B) demonstrate that the marker generates only a thin artifact (blue arrow) extending just below the surface of the skin. The artifact does not produce any distortion in the image at the TOI, thereby allowing the interpreting physician to document that the TOI is a benign cyst (orange arrow).

Figure 4A:
FIG. 4A shows a coronal plane image of a breast with a marker of the invention placed thereon. Crosshairs indicate the location on the TOI in the breast.
Figure 4B:
FIG. 4B shows a coronal plane image of the breast in FIG. 4A with no tissue marker. Crosshairs indicate the location on the TOI in the breast.
Figure 4C:
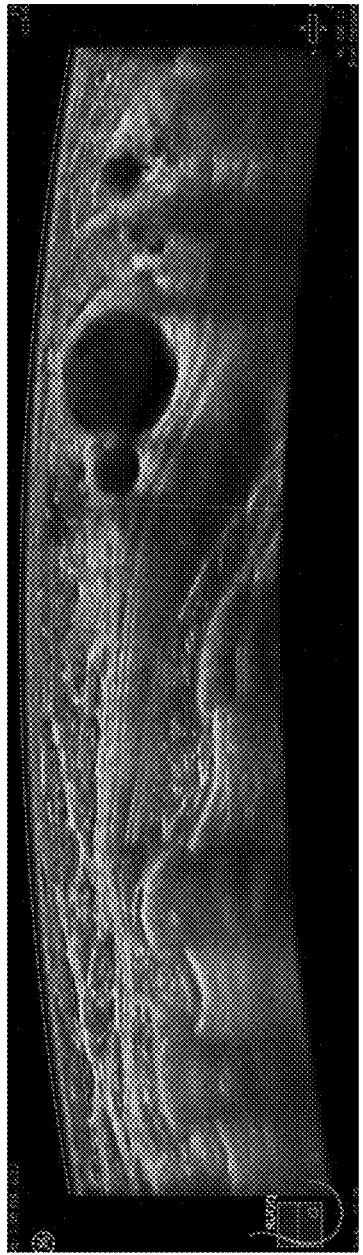
FIG. 4C shows a transverse or acquisition plane image of the breast in FIG. 4A with a marker of the invention placed thereon. Crosshairs indicate the location on the TOI in the breast.
Figure 4D:
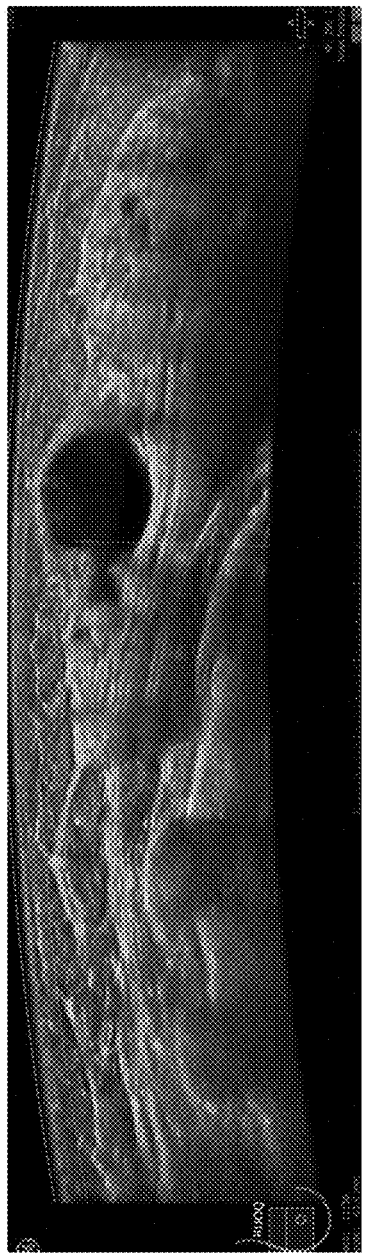
FIG. 4D shows a transverse or acquisition plane image of the breast in FIG. 4A without a marker. Crosshairs indicate the location on the TOI in the breast.

A side by side comparison of images of the breast with and without a marker placed thereon was performed. Coronal images of the breast with (FIG. 4A) and absent the marker (FIG. 4B), demonstrates that the marker was successful at clearly marking the area of interest. The transverse or acquisition plane image of the breast with the marker (FIG. 4C) demonstrates the minimal artifact produced by the marker when compared to the same tissue location in an image of the breast acquired without the marker (FIG. 4D). The marker does not obscure the TOI and does not interfere with the interpretation of the finding.

What is claimed is:

1. A method of documenting breast tissue of interest in a subject in need thereof using automated breast ultrasound, the method consisting of:
    a. placing a marker having a flat configuration with an upper side and a lower side at the surface of the breast at a location designating the breast tissue of interest, wherein the lower side of the marker is in contact with the surface of the breast;
    b. acquiring an ultrasonic 3-D volumetric image of the breast by applying sound waves to the breast including the marker and the breast tissue of interest;
    c. identifying a sonographic outline of the marker at the surface of the breast in the acquired image, wherein the outline results from artifacts produced by the marker of a portion of the sound waves applied to the breast;
    d. identifying the breast tissue of interest in the image in reference to the outline of the marker at the surface of the breast, wherein the tissue of interest is breast tissue underlying the surface of the breast at the location of the marker; and
    e. documenting the breast tissue of interest,
        wherein documenting the breast tissue of interest consists of identifying or diagnosing a malignant mass, a benign mass, dense breast tissue, scar tissue, irregular breast tissue, and bilateral masses, or combinations thereof.

2. The method of claim 1, wherein the tissue of interest comprises a palpable mass.

3. The method of claim 1, wherein the subject is a human with dense breast tissue.

4. The method of claim 1, wherein the intensity of the outline of the marker at the surface of the breast in the acquired image is of uniform intensity.

5. The method of claim 1, wherein the artifacts result in an area of increased brightness in the acquired image.

6. The method of claim 1, wherein the marker comprises material uniformly distributed throughout the marker.

7. The method of claim 1, wherein the configuration of the marker comprises material, width, and thickness.

8. The method of claim 7, wherein the material of the marker is a plastic material.

9. The method of claim 8, wherein the width of the marker ranges from 0.3 cm to 1 cm.

10. The method of claim 8, wherein the marker is in the form of a circle, and the diameter of the circle ranges from 0.3 cm to 1 cm.

11. The method of claim 8, wherein the thickness of the marker ranges from 0.5 mm to 2 mm.

12. The method of claim 1, wherein the marker further comprises means for retaining the marker in a fixed position at the surface of the breast.

13. A method of using a surface marker for documenting a palpable mass in breast tissue of a subject in need thereof using automated breast ultrasound, the method consisting of:
   a. placing a plastic marker having a flat configuration with an upper side and a lower side, a width ranging from 0.3 cm to 1 cm, and a thickness ranging from 0.5 mm to 2 mm, at the surface of the breast at a location designating the breast tissue of interest, wherein the lower side of the marker is in contact with the surface of the breast;
   b. acquiring an ultrasonic 3-D volumetric image of the breast by applying sound waves to the breast including the marker and the breast tissue of interest;
   c. identifying a sonographic outline of the marker at the surface of the breast in the acquired image, wherein the outline of the marker results from artifacts produced by the marker of a portion of the sound waves applied to the breast;
   d. identifying the breast tissue of interest in the image in reference to the outline of the marker at the surface of the breast, wherein the tissue of interest is breast tissue underlying the surface of the breast at the location of the marker; and
   e. documenting the breast tissue of interest
      wherein documenting the breast tissue of interest consists of identifying or diagnosing a malignant mass, a benign mass, dense breast tissue, scar tissue, irregular breast tissue, and bilateral masses, or combinations thereof.

14. A method of using a surface marker for documenting a palpable mass in breast tissue of a subject in need thereof using automated breast ultrasound, the method consisting of:
   a. placing a circular plastic marker having a flat configuration with an upper side and a lower side, a diameter ranging from 0.3 cm to 1 cm, and a thickness ranging from 0.5 mm to 2 mm, at the surface of the breast at a location designating the breast tissue of interest, wherein the lower side of the marker is in contact with the surface of the breast;
   b. acquiring an ultrasonic 3-D volumetric image of the breast by applying sound waves to the breast including the marker and the breast tissue of interest;
   c. identifying a sonographic outline of the marker at the surface of the breast in the acquired image, wherein the outline of the marker results from artifacts produced by the marker of a portion of the sound waves applied to the breast;
   d. identifying the breast tissue of interest in the image in reference to the outline of the marker at the surface of the breast, wherein the tissue of interest is breast tissue underlying the surface of the breast at the location of the marker; and
   e. documenting the breast tissue of interest;
      wherein documenting the breast tissue of interest consists of identifying or diagnosing a malignant mass, a benign mass, dense breast tissue, scar tissue, irregular breast tissue, and bilateral masses, or combinations thereof.

\* \* \* \* \*